(12) United States Patent
Dallavalle

(10) Patent No.: US 12,419,634 B2
(45) Date of Patent: Sep. 23, 2025

(54) SUTURING CATHETER AND RELATIVE SYSTEM FOR PERCUTANEOUSLY REDUCING MITRAL INSUFFICIENCY

(71) Applicant: Francesco Dallavalle, Castelcovati (IT)

(72) Inventor: Francesco Dallavalle, Castelcovati (IT)

(73) Assignee: 4 Cardiovascular Srl, Pisa (IT)

( * ) Notice: Subject to any disclaimer, the term of this patent is extended or adjusted under 35 U.S.C. 154(b) by 327 days.

(21) Appl. No.: 17/995,151

(22) PCT Filed: Feb. 5, 2021

(86) PCT No.: PCT/IB2021/050948
§ 371 (c)(1),
(2) Date: Sep. 30, 2022

(87) PCT Pub. No.: WO2021/198799
PCT Pub. Date: Oct. 7, 2021

(65) Prior Publication Data
US 2023/0149011 A1 May 18, 2023

(30) Foreign Application Priority Data

Apr. 2, 2020 (IT) .......................... 102020000006994

(51) Int. Cl.
*A61B 17/04* (2006.01)
*A61B 17/00* (2006.01)

(52) U.S. Cl.
CPC ..... *A61B 17/0469* (2013.01); *A61B 2017/00243* (2013.01); *A61B 17/0467* (2013.01);
(Continued)

(58) Field of Classification Search
CPC .... A61B 2017/00243; A61B 2017/047; A61B 2017/0472; A61B 2017/0475
See application file for complete search history.

(56) References Cited

U.S. PATENT DOCUMENTS

| 2003/0181924 A1 | 9/2003 | Yamamoto et al. |
| 2007/0010829 A1* | 1/2007 | Nobles ............... A61B 17/0491 |
| | | 606/148 |

(Continued)

OTHER PUBLICATIONS

International Search Report and Written Opinion for International Patent Application No. PCT/IB2021/050948, mailed Mar. 16, 2021, 12 pages.

*Primary Examiner* — Tan-Uyen T Ho
*Assistant Examiner* — Cherie M Poland
(74) *Attorney, Agent, or Firm* — Armstrong Teasdale LLP

(57) ABSTRACT

A suturing catheter for reducing mitral insufficiency by applying suturing points percutaneously is provided. The suturing catheter has a catheter body provided with a distal end and at least one internal lumen, at least one U-folded suture filament with two free ends, each provided with a suture needle, a pair of stylets, each provided with a catch needle, the suture and catch needles being provided with a connecting portion that allows a catch needle to mechanically engage with a suture needle, and a lever having a stapling arm, from which the suture needles protrude. The stapling arm, together with the catheter body, from which the catch needles protrude, defines a catch zone for a flap of a mitral valve. An opposite operating arm, together with the catheter body, defines an operating zone of the lever.

11 Claims, 8 Drawing Sheets

(52) U.S. Cl.
CPC . *A61B 2017/047* (2013.01); *A61B 2017/0472* (2013.01); *A61B 2017/0475* (2013.01)

(56) References Cited

U.S. PATENT DOCUMENTS

| | | |
|---|---|---|
| 2011/0190793 A1 | 8/2011 | Nobles et al. |
| 2012/0041453 A1 | 2/2012 | Klingenbeck |
| 2019/0150903 A1* | 5/2019 | Nobles ............... A61B 17/0482 |

* cited by examiner

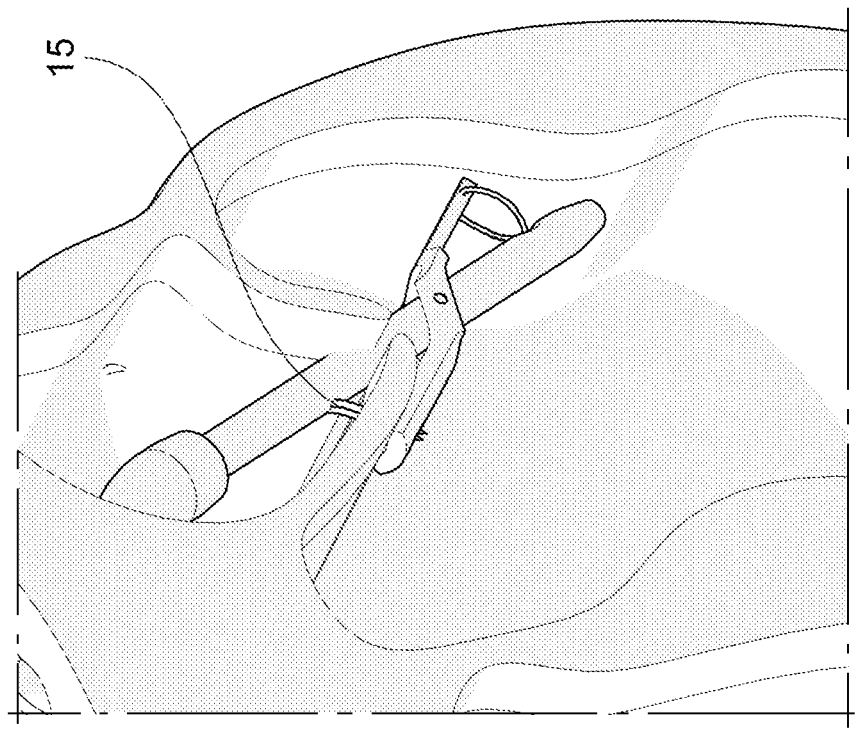
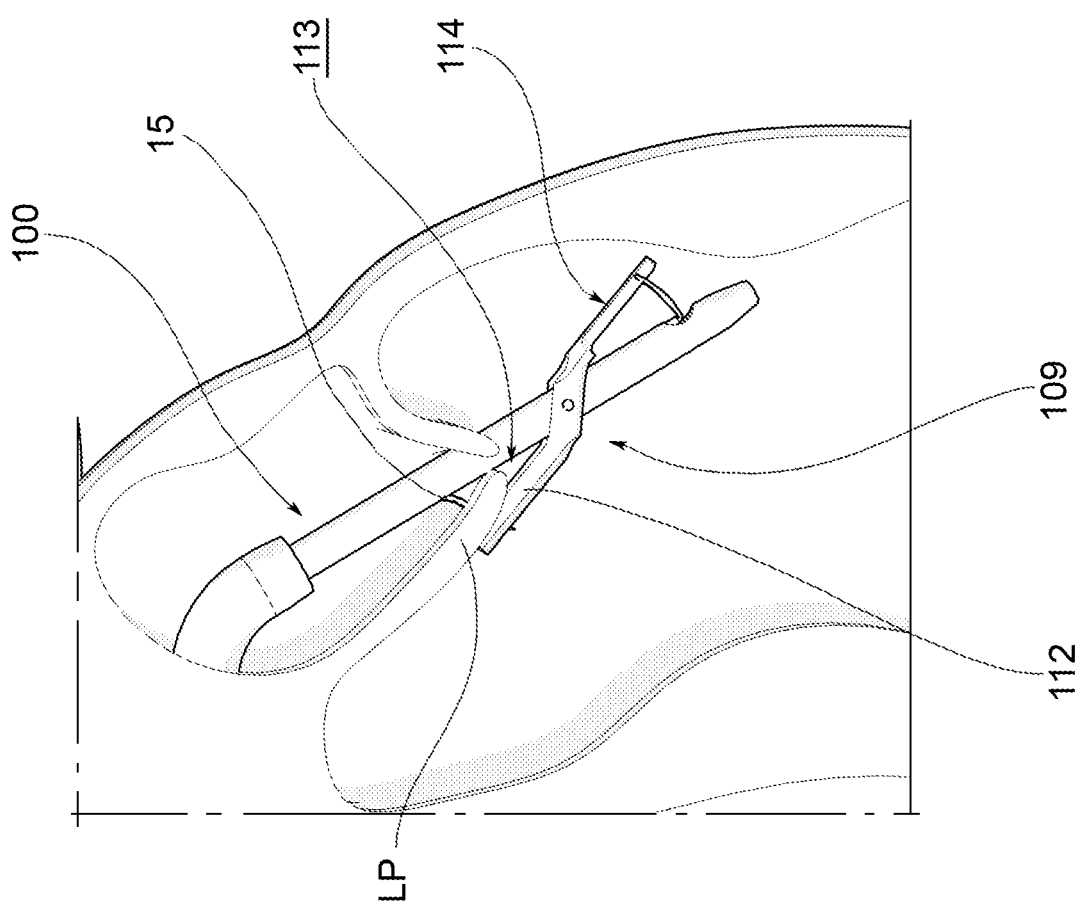
FIG.2a
FIG.2b

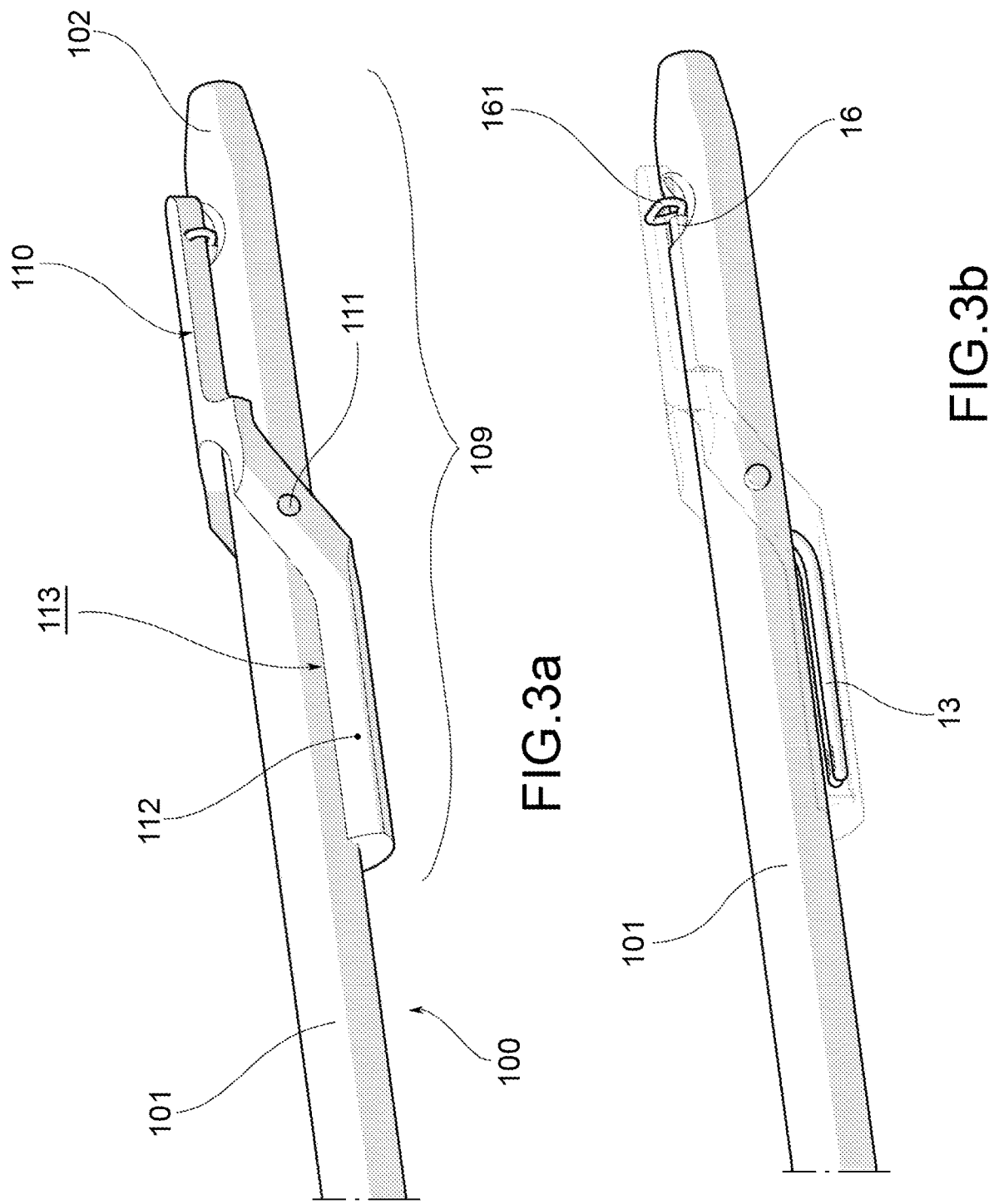

SUTURING CATHETER AND RELATIVE SYSTEM FOR PERCUTANEOUSLY REDUCING MITRAL INSUFFICIENCY

CROSS-REFERENCE TO RELATED APPLICATION

This application is a National Stage Application of International Patent Application No. PCT/IB2021/050948, having an International Filing Date of Feb. 5, 2021, which claims priority to Italian Application No. 102020000006994, filed Apr. 2, 2020, the entire contents of each of which are incorporated by reference herein.

FIELD OF THE INVENTION

It is the object of the present invention a suturing catheter for reducing mitral insufficiency by applying a suturing point percutaneously, and a relative system for reducing mitral insufficiency by applying suturing points ("edge to edge" technique) percutaneously.

BACKGROUND OF THE INVENTION

Mitral valve insufficiency is a heart disease which affects the mitral valve, one of the four valves located within the heart, whose function is to regulate the passage of blood between the left atrium and the left ventricle. The mitral valve is formed by two flaps, a posterior one (thicker) and an anterior one, attached to a base (mitral ring) and the free edges of the flaps are subtended by the tendon cords attached to the papillary muscles.

In physiological conditions, during the diastolic phase of filling the ventricle, the blood flows from the left atrium to the left ventricle by virtue of the opening of the mitral valve. During the systolic phase, when the ventricle contracts and empties, the mitral valve promptly closes, preventing a reflux of blood from the left ventricle to the left atrium.

When the mitral valve does not properly close during the phase of emptying the left ventricle, then part of the blood flows back to the left atrium, and this is called mitral valve insufficiency.

Moderate-severe mitral insufficiency is traditionally tackled with open heart surgery, since the disease, in addition to being disabling (causing dyspnea due to exertion, palpitation, reduced functional capacity), has a high mortality, equal to 5% per year.

Surgical correction of mitral insufficiency may be based on different techniques, including, for example, "edge to edge" technique, developed by Prof. Ottavio Alfieri. This is an operation in which the two mitral flaps are joined in the central portions thereof, with a suturing point (the so-called "Alfieri stitch") causing the formation of a double exit mitral valve.

For some years now, a technique has been developed to repair the mitral valve percutaneously, with an "edge to edge" technique, without the need for a conventional surgery with chest opening, cardiac arrest, extracorporeal circulation. The technique is based on the use of a small metal prosthesis which is positioned in the heart by means of a complex control system, under the guidance of transesophageal angiography, radioscopy and echocardiography. An example of such a prosthesis is shown in US patent document 2012/0041453 A1.

The use of such prostheses or clips, however, has some drawbacks: in some cases, it is not possible to position the clip since the flaps are too damaged; usually, it is not possible to place more than one clip, corresponding to a single suturing point; furthermore, in case of incorrect positioning, it is not possible to remove the clip.

Suturing catheters are known in the sector for reducing mitral insufficiency by percutaneously applying suturing points, shown, for example, in the documents US 2019/0150903 A1 or US 2011/190793 A1.

SUMMARY OF THE INVENTION

It is the object of the present invention to provide a system for reducing mitral insufficiency which is simple and safe.

In particular, it is the object of the present invention to provide a system for reducing mitral insufficiency by percutaneously applying suturing points with an "edge to edge" technique.

And again, it is the object of the present invention to provide a system for reducing mitral insufficiency capable of providing at least one suturing point even on very deteriorated mitral flaps, as well as providing more suturing points when required, and also to allow the removal of any suturing points badly positioned, all percutaneously.

Such an object is achieved by a suturing catheter for reducing mitral insufficiency by applying at least one suturing point percutaneously and a system for reducing mitral insufficiency by applying suturing points ("edge to edge" technique) percutaneously as described and claimed herein. Preferred embodiments of the present invention are also described.

BRIEF DESCRIPTION OF THE FIGURES

The features and advantages of the catheter and of the system for reducing mitral insufficiency according to the present invention will become apparent from the following description, given by way of a non-limiting example, in accordance with the accompanying drawings, in which:

FIG. 2A shows the suturing catheter of FIG. 1A in a step of applying a suturing point on a flap of the mitral valve;

FIG. 2B shows the suturing catheter of FIG. 2A, with a different angle, to better show the application of the suturing point;

FIG. 3A shows the suturing catheter in accordance with the present invention, in a closed advancement configuration;

FIGS. 3B to 3D show in detail the constituent components of the suturing catheter of FIG. 3A;

DETAILED DESCRIPTION

Figure 1A:
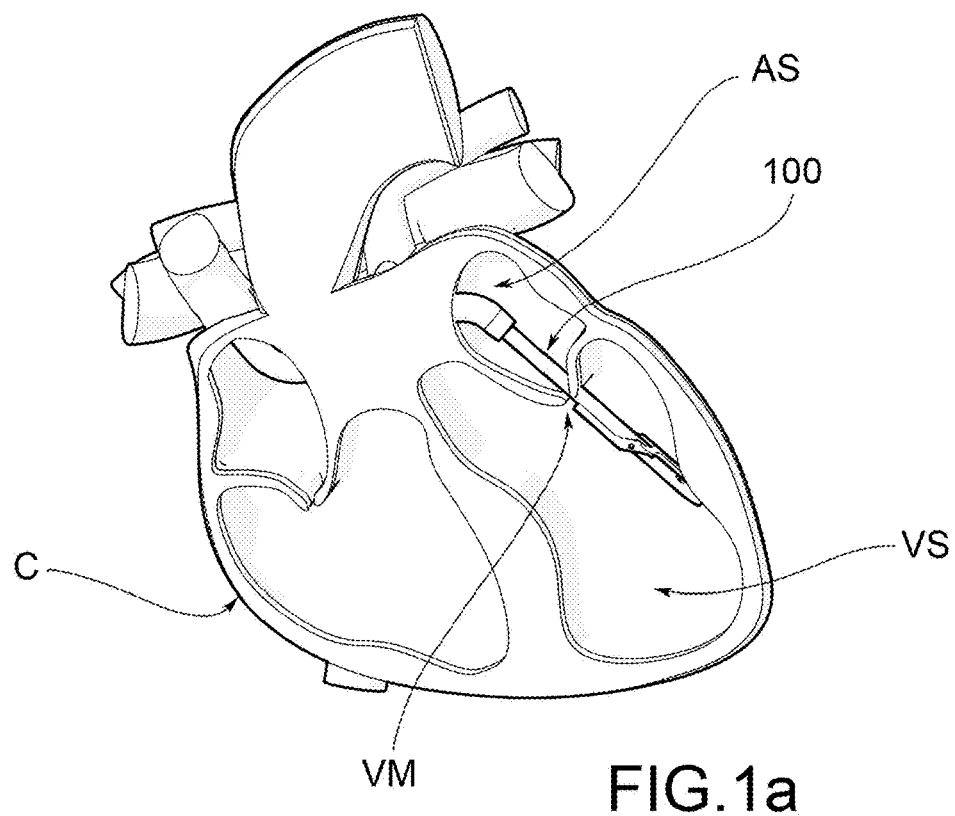
FIG. 1A shows a sectional view of a heart in which a component of the system for reducing mitral insufficiency according to the present invention is inserted, in particular, a suturing catheter in a positioning step.

FIG. 1A shows a sectioned heart C in which there is a defect of the mitral valve VM whose function is to regulate the passage of blood between the left atrium AS and the left ventricle VS. The mitral valve formed of two flaps, a posterior one, referred to as LP (larger), and an anterior one, referred to as LA.

The system for reducing mitral insufficiency according to the present invention comprises at least one pair of suturing catheters 100 as shown in FIGS. 1A to 4D.

The suturing catheter 100 comprises a catheter body 101 which extends between a proximal end (not shown) and a distal end 102.

Preferably, the distal end 102 is closed, and possibly rounded and/or tapered to avoid damaging or puncturing the heart tissue during the step of advancing the suturing catheter 100 up to the working position of FIG. 1A.

Figure 3C:
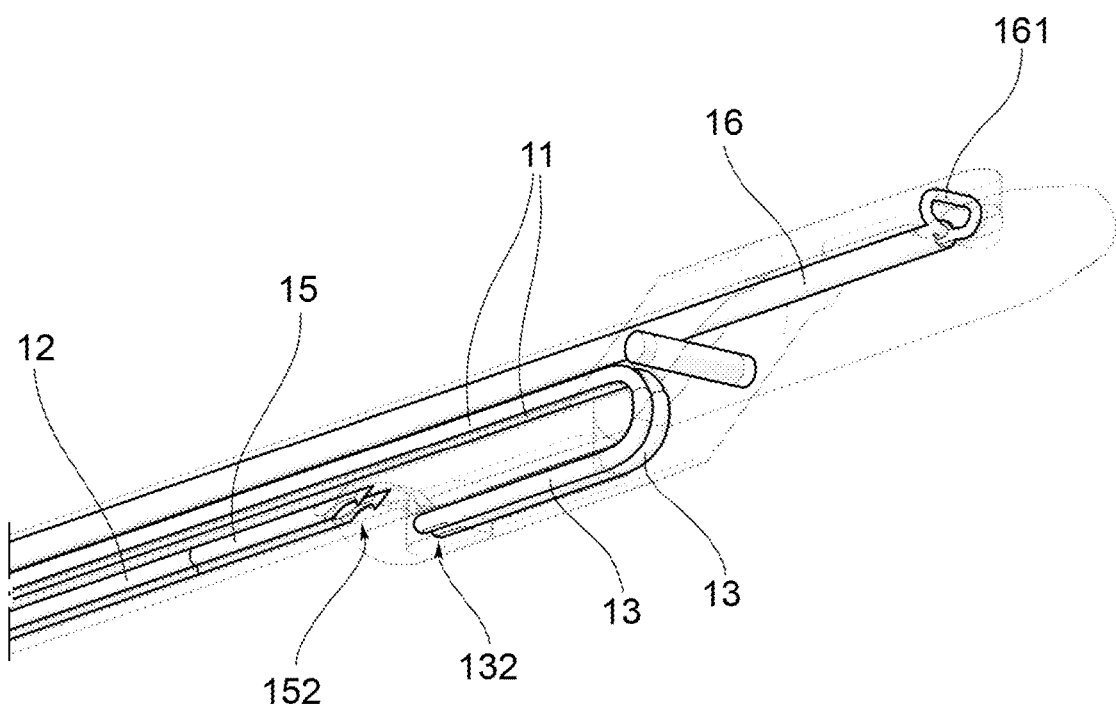
Figure 3D:
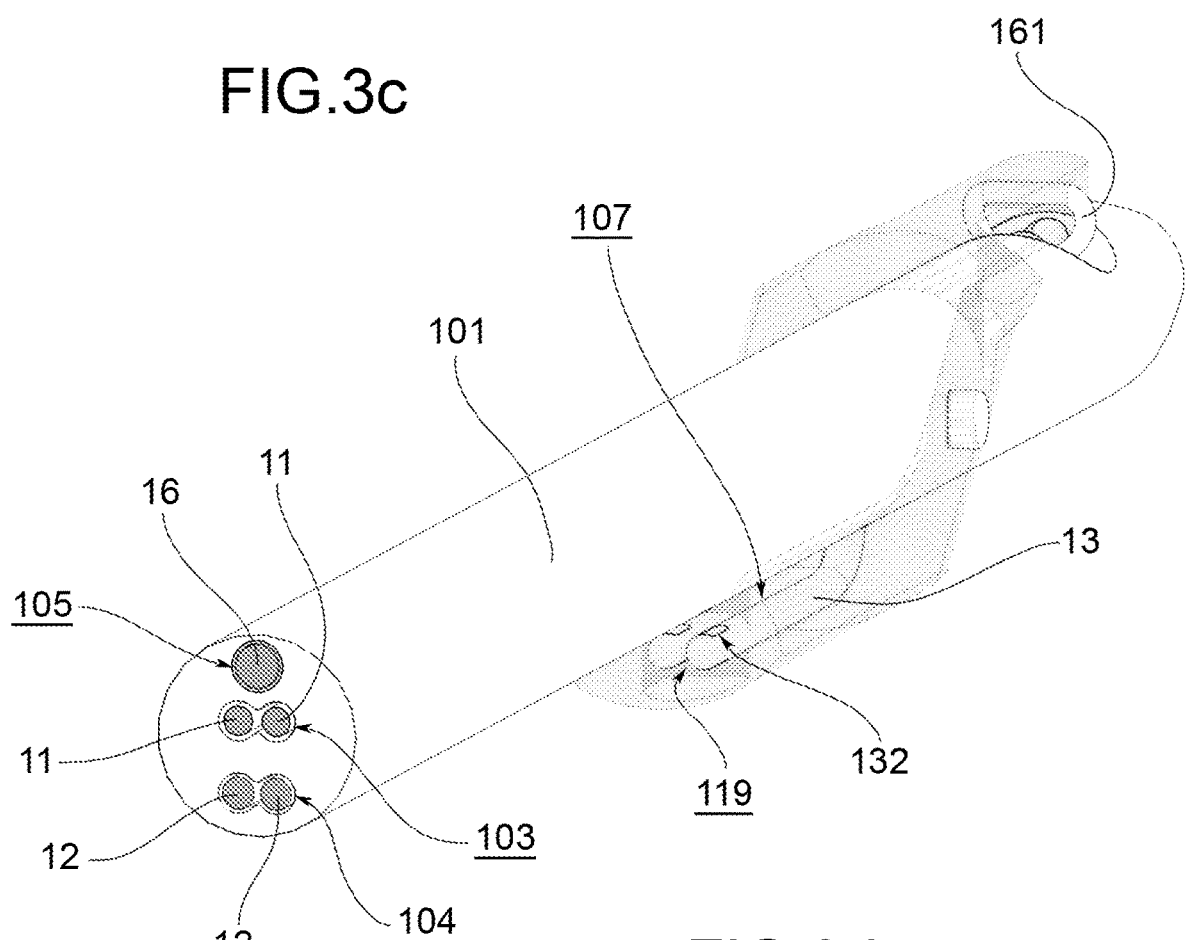

The catheter body 101 is provided with at least one internal lumen, defined as a suture lumen 103, adapted to receive a suture filament 1 that can slide therein, as shown in FIG. 3D.

In particular, the suture filament 1 is folded into a "U", with the joining portion (not shown) towards the proximal end of the catheter body 101, and the two free ends 11 towards the distal end of the catheter body 101.

Therefore, as it may be seen in FIG. 3D, the two free ends 11 of the same suture filament 1, joined together further downstream, slide parallel inside the suture lumen 103.

As shown in FIG. 3C, the two free ends 11 of the suture filament 1 are arranged inside the catheter body 101 in a distal position. Each free end 11 of the suture filament 1 is connected to a suture needle 13. Therefore, the suture filament 1 is connected to a pair of suture needles 13.

Preferably, suture needles 13 are elastic and flexible, made of nitinol and therefore with a shape memory, and have a rectilinear course.

The catheter body 101 is also provided with an internal lumen, defined as a catch lumen 104, adapted to receive a pair of stylets 12 that can slide therein, as shown in FIG. 3D.

Therefore, as it may be seen in FIG. 3D, the two stylets 12 slide parallel inside the catch lumen 104.

As shown in FIG. 3C, the distal ends of the stylets 12 are arranged inside the catheter body 101 in the distal position. The distal ends of the stylets are connected to a respective catch needle 15. Therefore, inside the catheter body 101, a pair of catch needles 15 is arranged in a distal position.

Preferably, the suture lumen 103 has a substantially eight-shaped or slot-shaped section. Such shape allows suture needles 13 to be kept in the correct position, i.e., side by side and facing each other at the respective catch needles 15 (as shown in FIG. 3C), and at the same time allows the sliding of the U-shaped connecting portion of the suture filament 1.

The catch lumen 104 has a substantially eight-shaped, or oval-shaped, section, and simultaneously receives both stylets 12.

In an embodiment variant not shown, the catheter body 101 is provided with a pair of parallel catch lumens 104, each adapted to receive a respective stylet 12, sliding therein.

It is therefore important that the suture lumen 103 and the catch lumen 104 run parallel inside of the catheter body 101 (as shown in FIG. 3D). In other words, it is important that the plane on which the axes of the two free ends 11 of the suture filament 1 lie is parallel to the plane on which the axes of the stylets 12 lie.

Figure 4A:
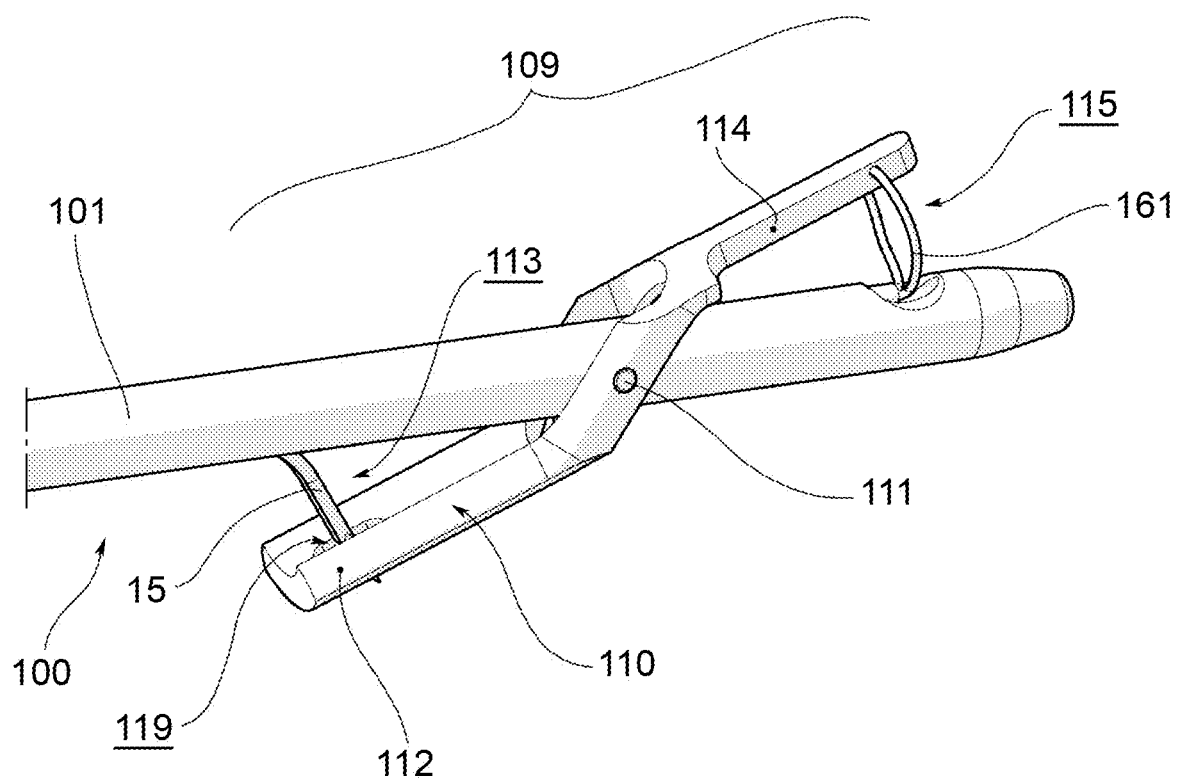
FIG. 4A shows the suturing catheter in accordance with the present invention, in a configuration for applying a suturing point.
Figure 4B:
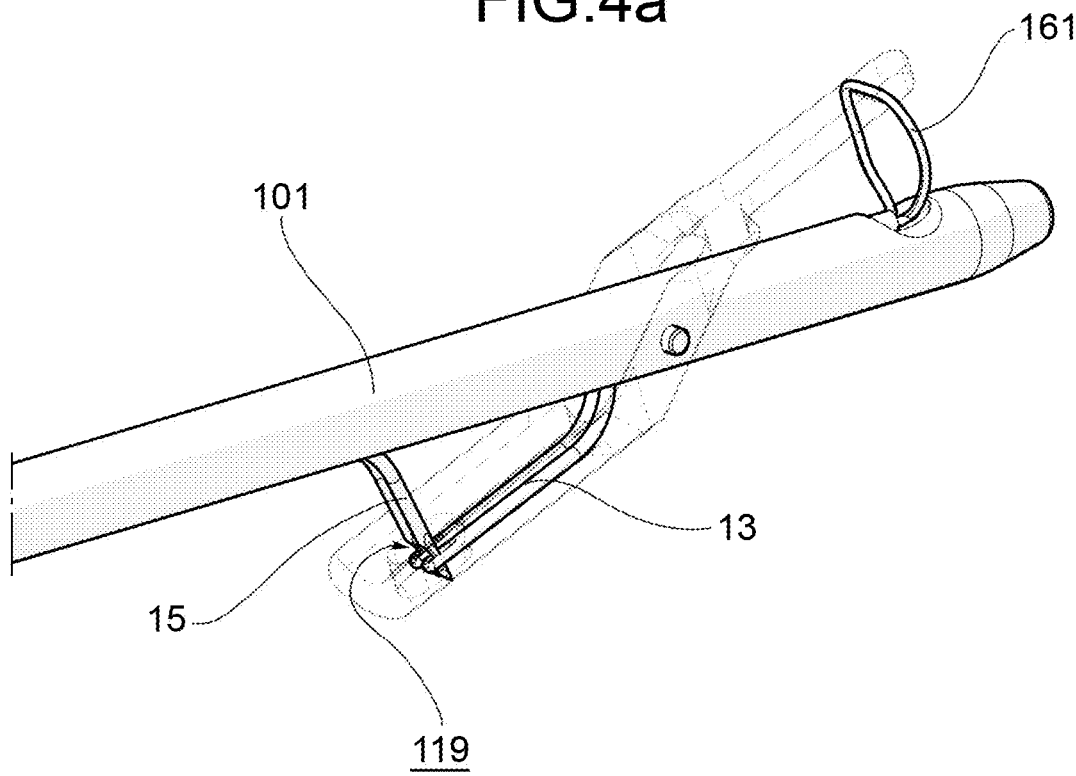
FIGS. 4B to 4D show in detail the constituent components of the suturing catheter of FIG. 4A.
Figure 4C:
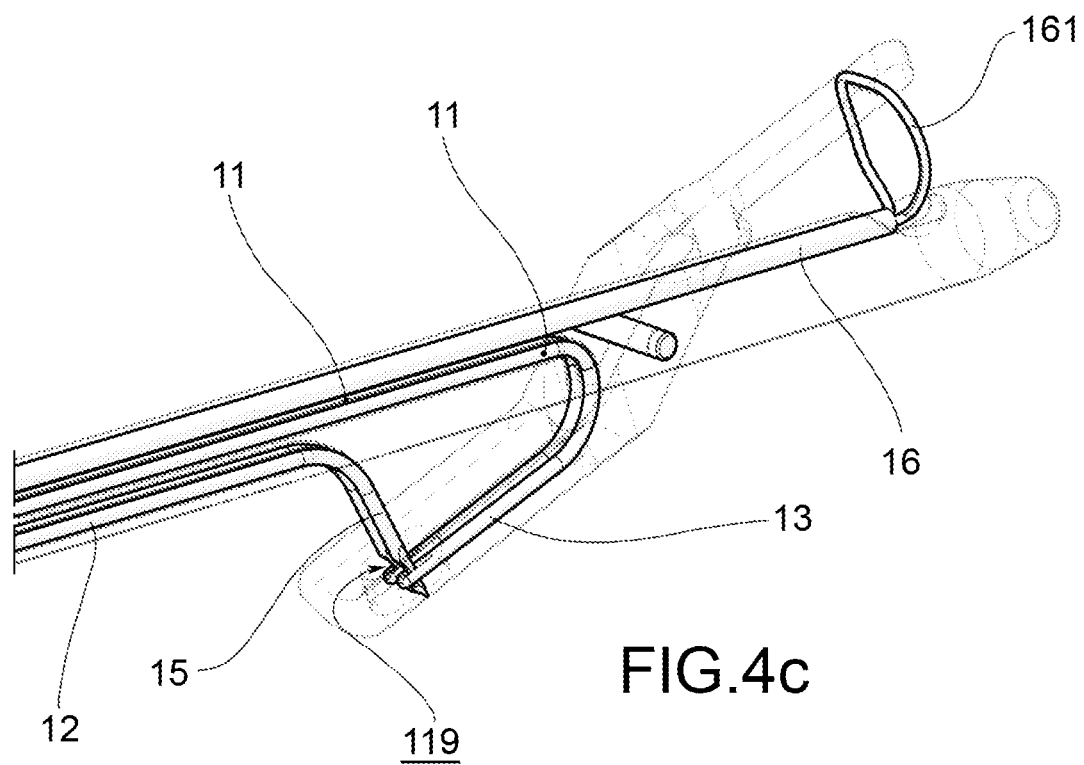
Figure 4D:
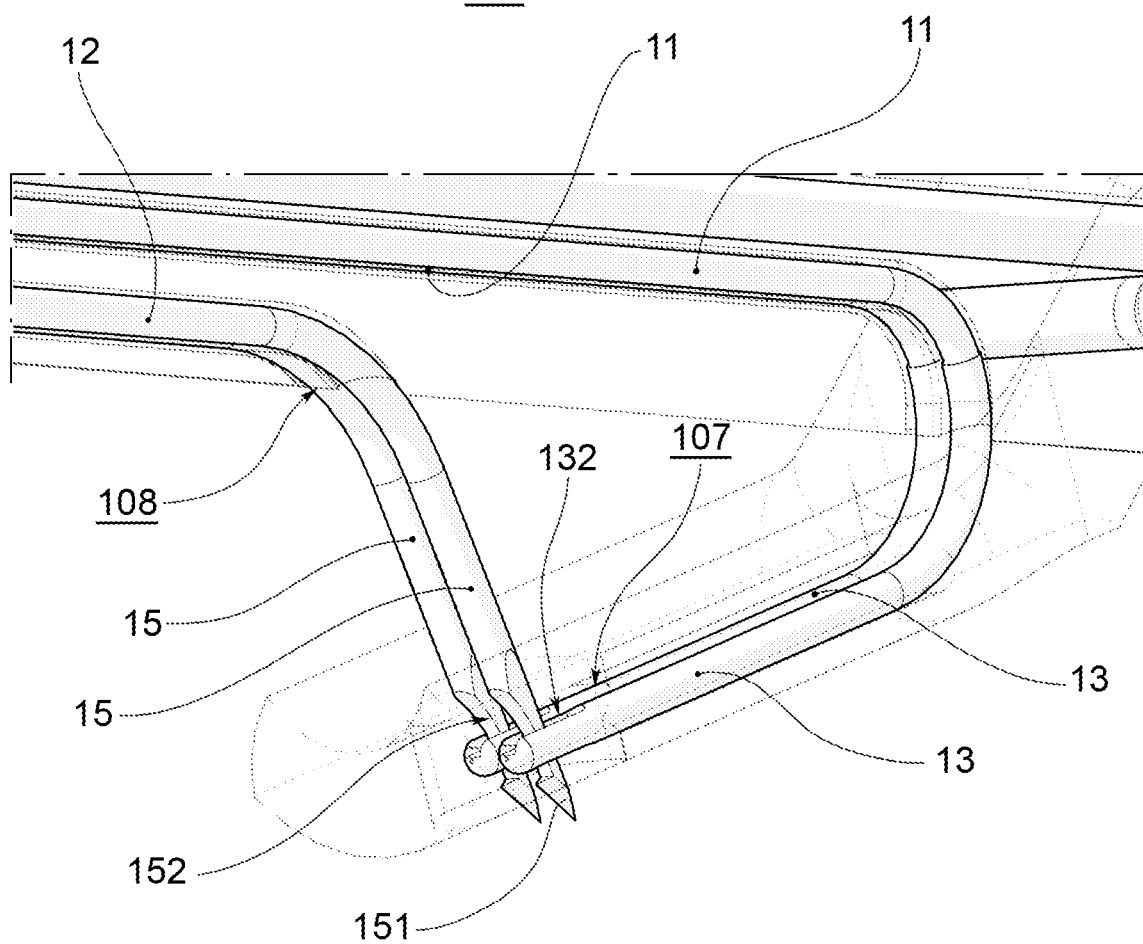

As it may be noticed in FIG. 4D, the catch needles 15 are provided, at the ends thereof, with a piercing tip 151 adapted to pierce a flap of the mitral valve.

Both the catch needles 15 and the suture needles 13 are provided, at the free ends thereof, with a connecting portion adapted to allow a catch needle 15 to mechanically engage with a respective suture needle 13 (as shown in FIG. 4D).

The suture needles 13 have a connecting portion 132 preferably in the form of a through hole, or slot, or groove. The catch needles 15 have a connecting portion 152 preferably in the form of a harpoon, or hook.

Back to FIG. 3A, the suture catheter 100 comprises, at the distal portion, a lever 110 connected to the catheter body 101 by means of a pin 111 which forms the fulcrum of the lever 110. Therefore, the catheter body 101, together with the lever 110, define a staple structure 109 for the suturing catheter 100.

The lever 110 comprises a stapling arm 112 which, together with the catheter body 101, defines a catch zone 113 of a flap of the mitral valve.

Preferably, the suture lumen 103 at least partially extends also inside the stapling arm 112. Therefore, the suture lumen 103 has an initial rectilinear course inside the catheter body 101, a curvilinear course in the passage zone towards the lever 110, and a final, again rectilinear, course inside the stapling arm 112. It should be noted that the suture needles 13 are arranged inside the stapling arm 112 and at least partially at the curve of the suture lumen 103 (FIG. 3C).

The stapling arm 112 is provided with an engagement opening 119, in the form of a through hole, preferably in the form of a slot. At the engagement opening 119, the connecting portions of the catch needles 15 and of the suture needles 13 meet, engaging with each other (as shown in FIG. 4D).

The suture lumen 103 ends in a distal outlet 107, obtained in the stapling arm 112, at the engagement opening 119. The catch lumen 104 ends in a distal outlet 108 obtained in the catheter body 101, which faces the engagement opening 119.

The suturing catheter 100 therefore comprises two suture needles 13 (parallel) and two catch needles 15 (parallel) contained inside a respective channel (suture lumen 103 and catch lumen 104) which is open towards the engagement opening 119.

The lever 110 further comprises an opposite operating arm 114 which, together with the catheter body 101, defines an operating zone 115 of the staple 109.

Preferably, the catch zone 113 is arranged in a position close to the fulcrum 111 and/or to the operating zone 115.

The catheter body 101 is also provided with an internal lumen, defined as a control lumen 105, adapted to receive a control mandrel 16 that can slide therein, as shown in FIG. 3D.

Preferably, the control lumen 105 has a substantially circular section.

As shown in FIG. 3C, the distal end of the control mandrel 16 is arranged inside the catheter body 101 in the distal position. Such distal end of the control mandrel 16 is connected, by means of a joining means 161, to the operating arm 114 of the lever 110. By retracting the control mandrel 16, the operating arm 114 is dragged into the closing position of the staple 109. By advancing the control mandrel 16, the operating arm 114 is pushed by the joining means 161 into the opening position of the staple 109.

Preferably, the joining means 161 is a relatively rigid loop engaged with the operating arm 114. Such solution is preferable, since the traction forces on the operating arm 114 are better distributed.

In an alternative example, the joining means is a traction wire engaged with the operating arm 114.

The operating arm 114, and consequently the staple structure 109 of the suturing catheter 100, may be operated by means of the control mandrel 16 between a closing position (as in FIG. 3A) and an opening position (as in FIG. 4A).

Figure 1B:
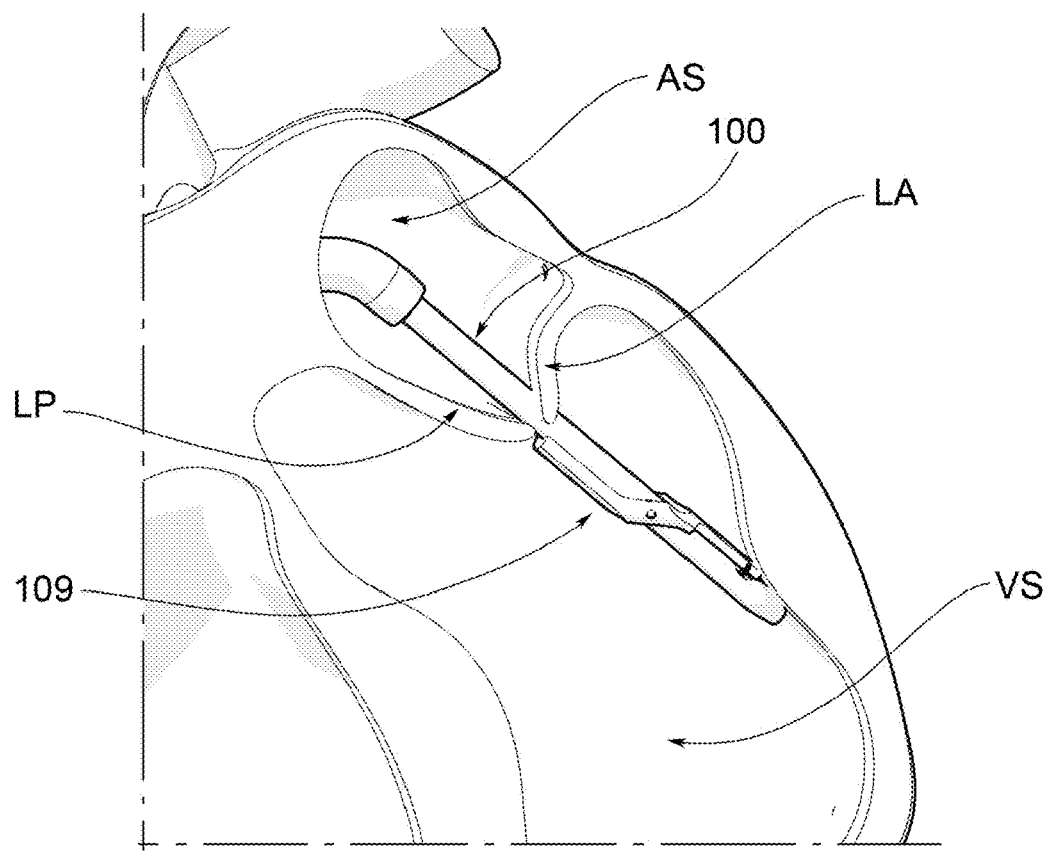
FIG. 1B shows a detail of FIG. 1A, in particular, the approaching of the suturing catheter towards a flap of the mitral valve.

In use, the suturing catheter 100 is advanced with staple 109 in the closing position (FIG. 1B). Once the zone to be treated is reached, the control mandrel 16 is advanced so as to push the operating arm 114 of the lever 110 towards the opening configuration of the staple 109 (FIG. 4A). It should be noted that the operating arm 114 of the lever 110 is pushed towards the opening configuration of the staple 109 also by the blood flow and by the elastic force of the suture needles 13 which, when resting, have a rectilinear configuration, and are now forced inside of the curvilinear portion of the suture lumen 103.

The suturing catheter 100, with the staple 109 open, is retracted until it catches a flap LP of the mitral valve inside the catch zone 113. By retracting the control mandrel 16, the operating arm 114 of the lever 110 is dragged towards the closing configuration of the staple 109 so as to pinch and firmly hold the flap LP of the mitral valve inside the catch zone 113.

At this point, the distal outlet 107 of the suture lumen 103 is aligned with the distal outlet 108 of the catch lumen 104. The catch needles 15 are advanced, pushing the respective stylets 12, so as to pierce, from side to side, the flap LP of the mitral valve. The catch needles 15 are advanced up to the inside of the engagement opening 119, in which they mechanically engage (by virtue of the harpoon shape thereof) with the respective suture needles 13 (FIG. 4A).

By retracting the stylets 12, and the catch needles 15 therewith, it is possible to drag the suture needles 13 inside the catch lumen 104, and also the suture filament 1 therewith, until the U-shaped joining portion of the filament itself is positioned on the mitral flap LP. A suturing point was thus obtained.

By virtue of the presence of the suture needles 13, the two free ends 11 of the suture filament 1 are inserted inside a microcatheter 20 (preferably a monorail one) which allows to remove the suturing catheter 100 without friction on the ends of the of suture filament 1.

The above operation is repeated so as to position a second suturing point on the opposite mitral flap LA, and possibly also a third or fourth suturing point, if required.

Figure 5A:
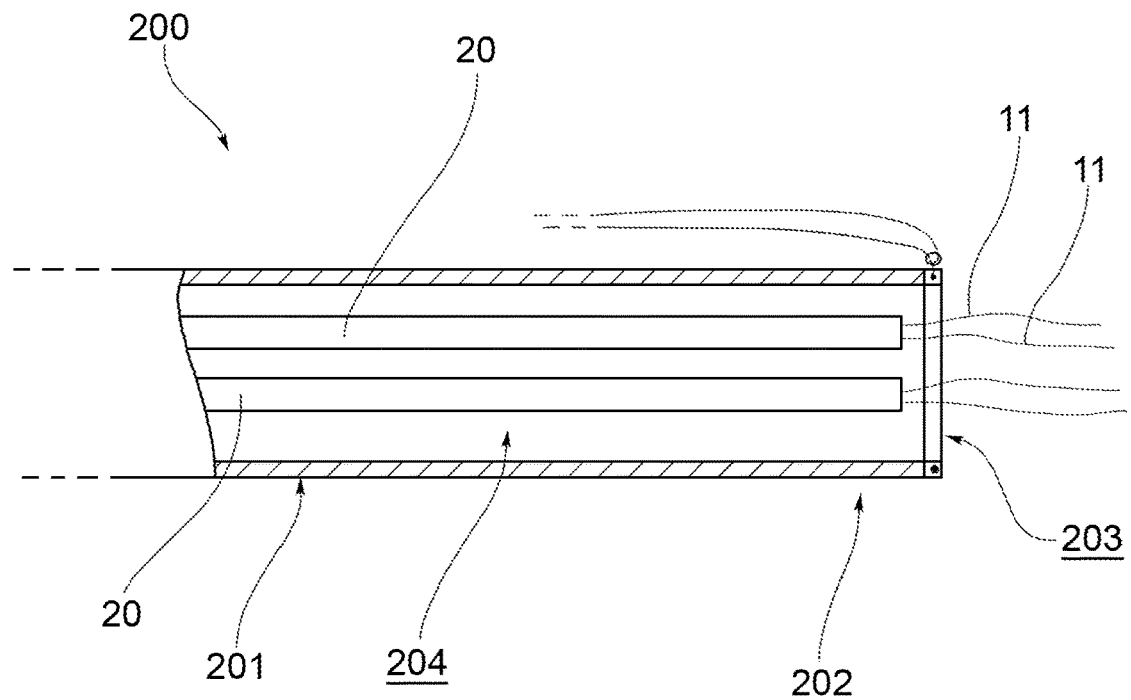
FIG. 5A shows a further component of the system for reducing mitral insufficiency according to the present invention, in particular, a knotting catheter for knotting suture filaments.
Figure 5B:
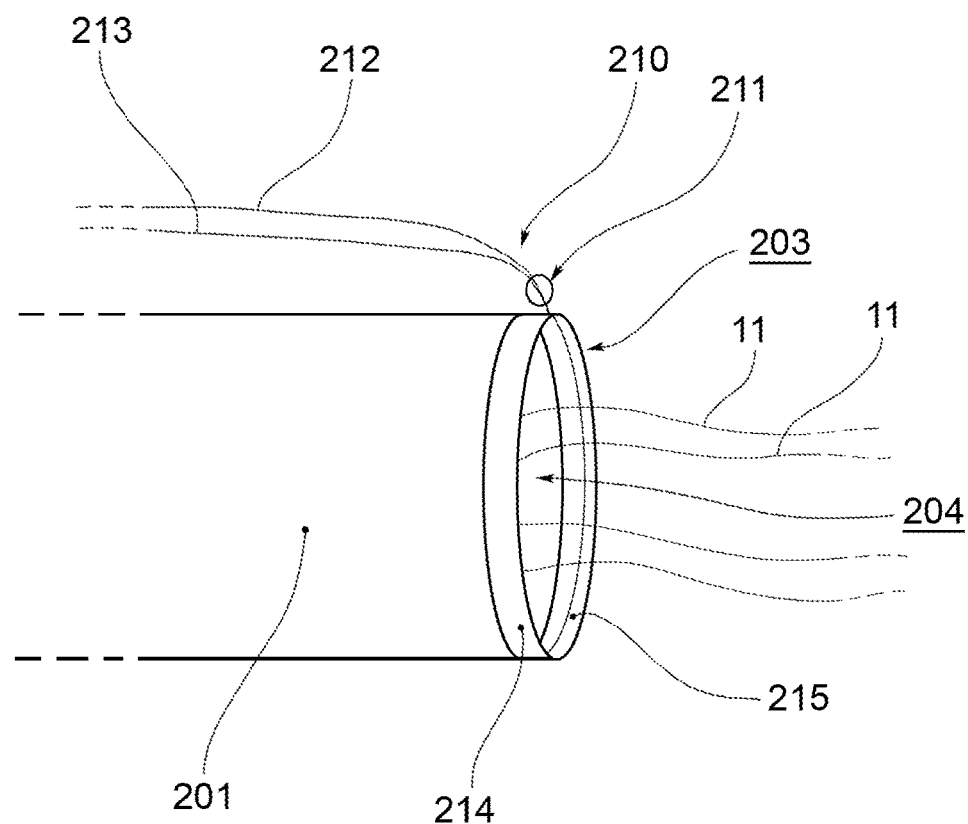
FIG. 5B shows a detail of the suture filaments of FIG. 5A.

Preferably, the system for reducing mitral insufficiency according to the present invention further comprises at least one knotting catheter 200 for knotting the suture filaments 1, shown in FIGS. 5A and 5B.

The knotting catheter 200 comprises a catheter body 201 which extends between a proximal end (not shown) and a distal end 202 which ends in a distal opening 203.

The catheter body 201 is provided with at least one internal lumen, defined as a containment lumen 204, adapted to receive, sliding therein, at least one microcatheter 20 in which the suture filament 1 forming the suturing point on the mitral flap LP, previously positioned with the suturing catheter 100, is accommodated.

At the distal end 202, preferably along the edge of the catheter body 201 defining the distal opening 203, a tightening filament 210 is accommodated, adapted to knot together the two free ends 11 of the suture filaments 1.

The tightening filament 210 comprises a loop (not shown, since it is accommodated inside a special seat 214), a slip knot 211, a constricting flap 212 that can reduce the diameter of the loop, and a fixing flap 213 that can tighten the slip knot 211. Preferably, the constricting flap 212 and the fixing flap 213 are different in terms of geometry, or surface, or color, so that they may be easily distinguished from each other.

The loop is accommodated in a seat 214, for example a ring-shaped seat, obtained on the edge of the catheter body 201 defining the distal opening 203.

The seat 214 is provided with an opening portion 215, also ring-shaped, obtained by pre-incision, or pre-cut, or weakening.

Preferably, the opening portion 215 faces towards the inside of the containment lumen 204.

During use, the microcatheters 20 containing the suture filaments 1 are inserted inside the knotting catheter 200. The distal end 202 of the knotting catheter 200 is approached to the valve flaps LP, LA on each of which at least one suturing point has been placed. By approaching the knotting catheter 200, and keeping the ends of the suture filaments 1 under tension, the mitral flaps are brought closer by reducing the section of the mitral valve and thus obtaining the desired effect of the Alfieri operation. During this step it is possible to evaluate the effectiveness of the section reduction, and possibly to modify it on the basis of the degree of residual insufficiency (by positioning the knotting catheter 200 more or less forward). Once the optimal residual section has been defined, the suture filaments are knotted together. In particular, by pulling the constricting flap 212 of the tightening filament 210, the diameter of the loop is reduced and comes out of the seat 214 through the opening portion 215. The diameter of the loop is reduced until all the suture filaments 1 are enclosed in a single bundle. At this point, by pulling the fixing flap 213 of the tightening filament 210, the slip knot 211 tightens to lock the loop in the position for tightening the suture filaments 1. Once the suture filaments 1 have been knotted, it is possible to remove the knotting catheter 200.

Figure 6:
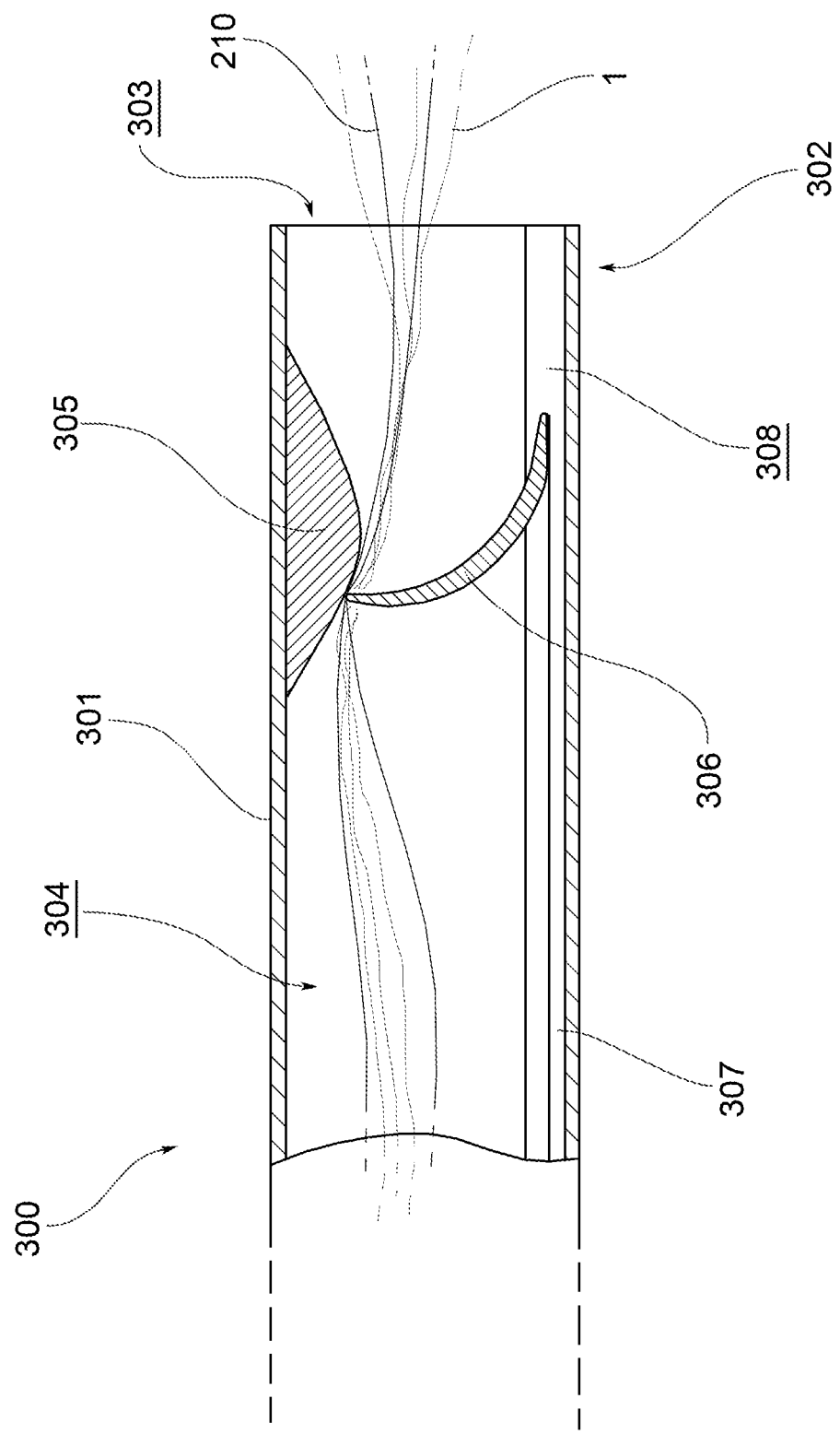
FIG. 6 shows a further component of the system for reducing mitral insufficiency according to the present invention, in particular, a cutting catheter for cutting suture filaments.

Preferably, the system for reducing mitral insufficiency according to the present invention further comprises at least one cutting catheter 300 for cutting the ends of the suture filaments 1 and of the tightening filament 210, shown in FIG. 6.

The cutting catheter 300 comprises a catheter body 301 which extends between a proximal end (not shown) and a distal end 302 which ends in a distal opening 303.

The catheter body 301 is provided with at least one internal lumen, defined as a main lumen 304, adapted to receive, sliding therein, the ends of the suture filaments 1 forming the suturing points on the mitral flap LP previously positioned with the suturing catheter 100, and the ends of the tightening filament 210.

Inside the main lumen 304, an abutment element 305 is accommodated, against which a blade 306 acts.

The catheter body 301 is provided with a further internal lumen, defined as a secondary lumen 308, adapted to receive a blade 306 and a relative operating mandrel 307.

In the resting configuration, the blade 306 is received inside the secondary lumen 308 so as not to interfere with the filaments sliding inside the main lumen 304. By retracting the operating mandrel 307, the blade 306 comes out of the secondary lumen 308 towards and inside the main lumen 304. The blade intercepts the filaments until pushing them in abutment against the abutment element 305 and therefore cuts the aforesaid filaments.

During use, the suture filaments 1 and/or the tightening filament 210 are inserted inside the cutting catheter 300. The distal end 302 of the cutting catheter 300 is approached to the valve flaps LP, LA until the desired position is reached. At this point, the blade 306 is operated to cut the aforesaid filaments.

Innovatively, a catheter and a system for reducing mitral insufficiency in accordance with the present invention is easy to use, safe and particularly effective.

Advantageously, a system for reducing mitral insufficiency in accordance with the present invention allows the treatment of mitral insufficiency by percutaneously applying suturing points with an "edge to edge" technique.

Advantageously, a catheter and a system for reducing mitral insufficiency in accordance with the present invention is capable of performing at least one suturing point even on very deteriorated mitral flaps.

Advantageously, a system for reducing mitral insufficiency in accordance with the present invention allows to position more suturing points on the same mitral flap when required.

Advantageously, a system for reducing mitral insufficiency in accordance with the present invention allows the removal of any badly positioned suturing points.

It is apparent that those skilled in the art may modify the object described above, without departing from the scope of protection as defined by the following claims.

What is claimed is:

1. A suturing catheter for reducing mitral insufficiency by applying suturing points percutaneously, comprising:
    a catheter body provided with a distal end and at least one internal lumen;
    at least one suture filament slidable in an internal lumen defined as a suture lumen, said at least one suture filament being U-folded with two free ends arranged at the distal end of the catheter body;
    a pair of suture needles, each of which is connected to a respective free end of the at least one suture filament;
    a pair of stylets slidable in an internal lumen defined as a catch lumen, each of which is provided with a distal end arranged at the distal end of the catheter body;
    a pair of catch needles, each of which is connected to a respective distal end of a respective stylet, wherein said catch needles and said suture needles are provided with a connecting portion that allows a catch needle to mechanically engage with a respective suture needle; and
    a lever connected to the distal end of the catheter body by a pin, said lever comprising:
        a stapling arm, containing said suture needles which, together with the catheter body containing said catch needles defines a catch zone for a flap of a mitral valve; and
        an opposite operating arm connected to a control mandrel by a joining means which, together with the catheter body, defines an operating zone of the lever.

2. The suturing catheter of claim 1, wherein said stylets slide in parallel inside a single catch lumen or slide in parallel inside separate catch lumens.

3. The suturing catheter of claim 1, wherein the suture lumen and/or the catch lumen has a portion substantially eight-shaped or slot-shaped.

4. The suturing catheter of claim 1, wherein the suture lumen and the catch lumen run in parallel inside the catheter body such that a plane on which the axes of the two free ends of the at least one suture filament lie is parallel to a plane on which the axes of the two stylets lie.

5. The suturing catheter of claim 1, wherein the suture needles comprise a connecting portion having a through-hole and the catch needles comprise a harpoon-shaped connecting portion.

6. The suturing catheter of claim 1, wherein at least part of the suture lumen also extends inside the stapling arm, the suture lumen initially having a curvilinear course thereby forming a curvilinear portion and ending with a rectilinear course, and wherein the suture needles are arranged in said curvilinear portion, at least in part.

7. The suturing catheter of claim 1, wherein the stapling arm is provided with an engagement opening, wherein the suture lumen leads to said engagement opening and the catch lumen faces said engagement opening, and wherein the connecting portion of the catch needles engages with the connecting portion of the suture needles in said engagement opening.

8. The suturing catheter of claim 1, wherein the joining means is a rigid loop engaged to the operating arm.

9. A system for reducing mitral insufficiency by applying suturing points percutaneously, the system comprising:
    at least one pair of suturing catheters according to claim 1, each positioning at least one suturing point on a flap of a mitral valve;
    at least one knotting catheter for knotting suture filaments that define the suturing points positioned by the suturing catheters; and
    at least one cutting catheter for cutting the suture filaments.

10. The system of claim 9, wherein said at least one knotting catheter comprises:
    a catheter body provided with a distal end and at least one internal containment lumen that ends in a distal opening;
    at least one tightening filament for knotting the suture filaments, said at least one tightening filament comprising a loop, a slip knot, a constricting flap suitable for reducing a diameter of the loop and a fixing flap suitable for tightening the slip knot; and
    a seat for said loop of the at least one tightening filament that is arranged in the distal opening in the catheter body, said seat being provided with an openable portion for the loop to exit when knotting the suture filaments.

11. The system of claim 9, wherein said at least one cutting catheter comprises:
    a catheter body having a distal end having at least one main internal lumen that ends in a distal opening; and
    a blade for cutting the suture filaments and/or the at least one tightening filament, the blade being operated by an operating mandrel.

* * * * *